(12) United States Patent
Picazo et al.

(10) Patent No.: US 8,337,913 B1
(45) Date of Patent: Dec. 25, 2012

(54) CLEANING SWABS FOR FINGERNAILS

(76) Inventors: Alejandra L. Picazo, Pasadena, CA (US); Michael S. Farraj, Pasadena, CA (US)

( * ) Notice: Subject to any disclaimer, the term of this patent is extended or adjusted under 35 U.S.C. 154(b) by 152 days.

(21) Appl. No.: 12/900,001

(22) Filed: Oct. 7, 2010

(51) Int. Cl.
*A61K 36/25* (2006.01)
*A61K 36/00* (2006.01)
*A01N 25/34* (2006.01)

(52) U.S. Cl. .......... 424/728; 424/725; 424/411
(58) Field of Classification Search .......... None
See application file for complete search history.

(56) References Cited

U.S. PATENT DOCUMENTS

| | | |
|---|---|---|
| 1,367,974 A | 2/1921 | Ivory |
| 1,667,570 A | 4/1928 | Thelander |
| 1,956,627 A | 5/1934 | Roth |
| 4,547,363 A * | 10/1985 | Joos .......... 424/61 |
| 4,886,078 A | 12/1989 | Shiffman |
| 4,930,529 A | 6/1990 | Whitney |
| 5,487,776 A * | 1/1996 | Nimni .......... 106/18.35 |
| D416,688 S | 11/1999 | Baltierra |
| 6,102,048 A | 8/2000 | Baker |
| 6,153,208 A * | 11/2000 | McAtee et al. .......... 424/402 |
| 6,342,208 B1 * | 1/2002 | Hyldgaard et al. .......... 424/59 |
| 6,516,812 B2 | 2/2003 | Chang |
| 6,676,952 B2 * | 1/2004 | Renimel et al. .......... 424/401 |
| 8,034,891 B2 * | 10/2011 | Okawa .......... 528/31 |
| 2007/0020220 A1 * | 1/2007 | Osborne .......... 424/70.14 |
| 2007/0113864 A1 | 5/2007 | Vera |
| 2007/0154575 A1 * | 7/2007 | Shimoda et al. .......... 424/756 |
| 2007/0172431 A1 * | 7/2007 | Galumbeck .......... 424/47 |
| 2008/0299060 A1 * | 12/2008 | Bruno et al. .......... 424/61 |
| 2009/0068128 A1 * | 3/2009 | Waddington .......... 424/59 |
| 2009/0183327 A1 | 7/2009 | Karie |
| 2009/0274770 A1 * | 11/2009 | Gammelsaeter et al. .......... 424/581 |
| 2011/0250227 A1 * | 10/2011 | Elraz .......... 424/195.17 |

* cited by examiner

*Primary Examiner* — Christopher R. Tate

(57) ABSTRACT

A cleaning swab for cleaning, disinfecting, and sealing underneath fingernails. The swab features an elongated shaft having a first end and a second end. A first absorbent component is disposed on the first end of the elongated shaft. The first absorbent component is impregnated with a solution with at least six of the following: keratin, equisetum arvense, carrageenan, aucoumea klaineana extract, ginseng root extract, vitamin C, and tea tree oil.

4 Claims, 3 Drawing Sheets

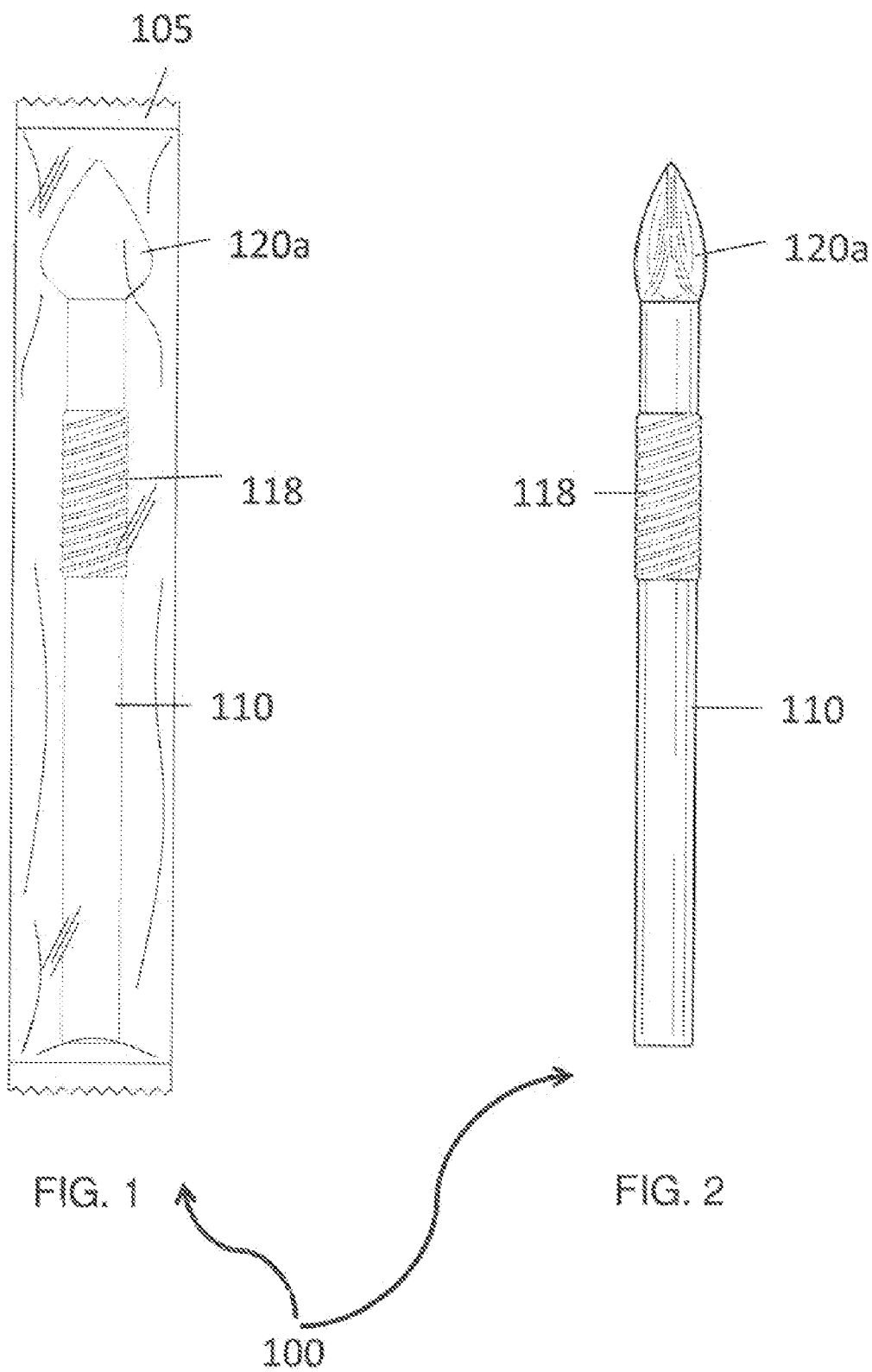

CLEANING SWABS FOR FINGERNAILS

FIELD OF THE INVENTION

The present invention is directed to a personal hygiene tool, more particularly to a cotton swap with a novel cleaning solution for cleaning, disinfecting, and sealing underneath fingernails.

BACKGROUND OF THE INVENTION

To clean under one's fingernails, individuals generally use a thin piece of metal or wood to scrap dirt from under the nail. The present invention features cleaning swabs with a novel cleaning solution for cleaning, disinfecting, and sealing underneath fingernails. The swabs of the present invention can help promote good personal hygiene as well as help prevent infections occurring in and around the fingernail. The swabs may be available (or used) in a variety of locations including but not limited to hospitals, vehicles, convenience stores, hospitality locations such as hotels and motels, nail salons, homes, work places, and the like. The swabs may be packaged in dispensers or individual packets (wrappers).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1 is a side view of a swab of the present invention as wrapped in a wrapper.

FIG. 2 is a side view of a swab of the present invention.

DESCRIPTION OF PREFERRED EMBODIMENTS

Figure 3:
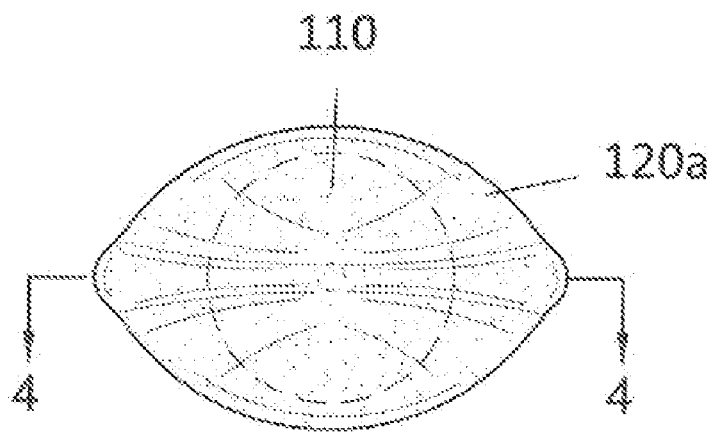
FIG. 3 is a top view of the swab of FIG. 2.

Referring now to FIGS. 1-5, the present invention features cleaning swabs 100 with a novel cleaning solution for cleaning, disinfecting, and sealing underneath fingernails. The swabs may be available (or used) in a variety of locations including but not limited to hospitals, vehicles, convenience stores, hospitality locations such as hotels and motels, nail salons, and the like. The swabs 100 may be packaged in dispensers or individual packets (wrappers 105).

The swabs 100 of the present invention comprise an elongated shaft 110 having a first end and a second end. A gripping component 118 may be disposed on the shaft 110, for example near the first end, in or around the middle, and/or near the second end. Disposed on at least the first end is a first absorbent component (e.g., cotton) 120a. The first absorbent component 120a is soaked with a solution 160 for cleaning, disinfecting, and sealing (e.g., helping to prevent accumulation of dirt, debris, and oil) underneath the fingernail.

In some embodiments the solution 160 comprises one or more (at least one) of the following: keratin (e.g., hydrolyzed keratin), horsetail extract (e.g., equisetum arvense), carrageenan, aucoumea klaineana extract, ginseng root extract, vitamin C (e.g., sodium ascorbyl phosphate), and tea tree (e.g., oil). In some embodiments the solution 160 comprises two or more (at least two) of the following: keratin (e.g., hydrolyzed keratin), horsetail extract (e.g., equisetum arvense), carrageenan, aucoumea klaineana extract, ginseng root extract, vitamin C (e.g., sodium ascorbyl phosphate), and tea tree (e.g., oil). In some embodiments the solution 160 comprises three or more (at least three) of the following: keratin (e.g., hydrolyzed keratin), horsetail extract (e.g., equisetum arvense), carrageenan, aucoumea klaineana extract, ginseng root extract, vitamin C (e.g., sodium ascorbyl phosphate), and tea tree (e.g., oil). In some embodiments the solution 160 comprises four or more (at least four) of the following: keratin (e.g., hydrolyzed keratin), horsetail extract (e.g., equisetum arvense), carrageenan, aucoumea klaineana extract, ginseng root extract, vitamin C (e.g., sodium ascorbyl phosphate), and tea tree (e.g., oil). In some embodiments the solution 160 comprises five or more (at least five) of the following: keratin (e.g., hydrolyzed keratin), horsetail extract (e.g., equisetum arvense), carrageenan, aucoumea klaineana extract, ginseng root extract, vitamin C (e.g., sodium ascorbyl phosphate), and tea tree (e.g., oil). In some embodiments the solution 160 comprises six or more (at least six) of the following: keratin (e.g., hydrolyzed keratin), horsetail extract (e.g., equisetum arvense), carrageenan, aucoumea klaineana extract, ginseng root extract, vitamin C (e.g., sodium ascorbyl phosphate), and tea tree (e.g., oil). Optionally, the solution 160 further comprises other proteins (e.g., peptides). Without wishing to limit the present invention to any theory or mechanism, it is believed that tea tree oil may help as an antibacterial and/or an antifungal component in the solution 160.

In some embodiments, the solution 160 comprises the following amino acids: Aspartic Acid (Asp), Glutamic Acid (Glu), Serine (Ser), Glycine (Gly), Histidine (His), Argenine (Arg), Threonine (Thr), Alanine (Ala), Proline (Pro), Tyrosine (Tyr), Valine (Val), Methionine (Met), Lanthionine (Lan), Isoleucine (Ile), Leucine (Leu), Phenylalanine (Phe), Lysine (Lys), and Cystine (Cys). In some embodiments, the percentage of Aspartic Acid (Asp) is between about 5 to 10%, for example 6.6%. In some embodiments, the percentage of Glutamic Acid (Glu) is between about 10 to 15%, for example 14.2%. In some embodiments, the percentage of Serine (Ser) is between about 10 to 15%, for example 10.7%. In some embodiments, the percentage of Glycine (Gly) is between about 5 to 10%, for example 8.3%. In some embodiments, the percentage of Histidine (His) is between about 0.1 to 5%, for example 0.7%. In some embodiments, the percentage of Argenine (Arg) is between about 5 to 10%, for example 7%. In some embodiments, the percentage of Threonine (Thr) is between about 5 to 10%, for example 6.4%. In some embodiments, the percentage of Alanine (Ala) is between about 5 to 10%, for example 7.3%. In some embodiments, the percentage of Proline (Pro) is between about 5 to 10%, for example 6.6%. In some embodiments, the percentage of Tyrosine (Tyr) is between about 0.5 to 5%, for example 1.6%.

In some embodiments, the percentage of Valine (Val) is between about 5 to 10%, for example 6.9%. In some embodiments, the percentage of Methionine (Met) is between about 0.01 to 1%, for example 0.1%. In some embodiments, the percentage of Lanthionine (Lan) is between about 0.1 to 5%, for example 0.5%. In some embodiments, the percentage of Isoleucine (Ile) is between about 1 to 5%, for example 3.8%. In some embodiments, the percentage of Leucine (Leu) is between about 5 to 10%, for example 8.8%. In some embodiments, the percentage of Phenylalanine (Phe) is between about 1 to 5%, for example 2.4%. In some embodiments, the percentage of Lysine (Lys) is between about 1 to 5%, for example 2.4%. In some embodiments, the percentage of Cystine (Cys) is between about 2 to 10%, for example 4.8%.

Figure 4:
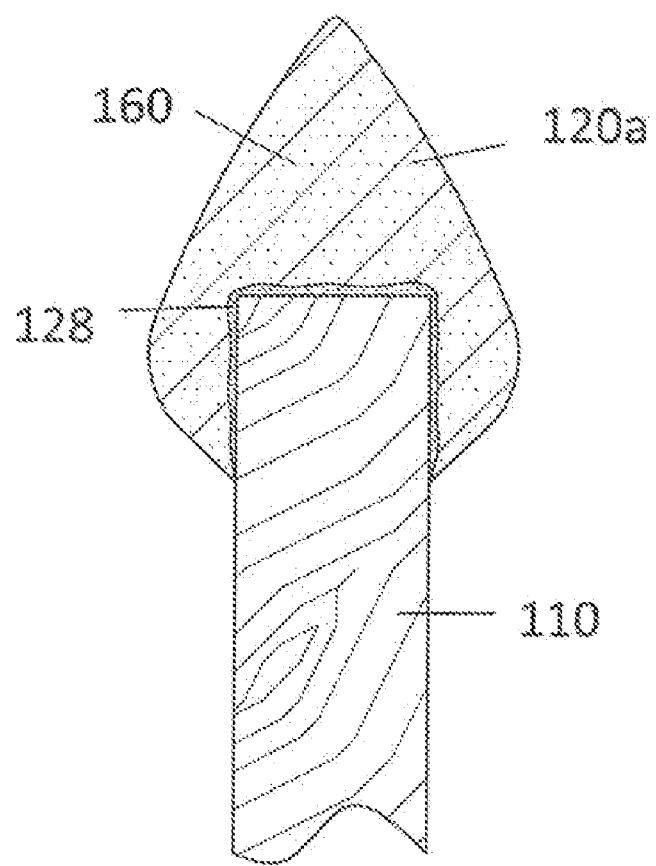
FIG. 4 is a cross sectional view of the swab of FIG. 3.
Figure 5:
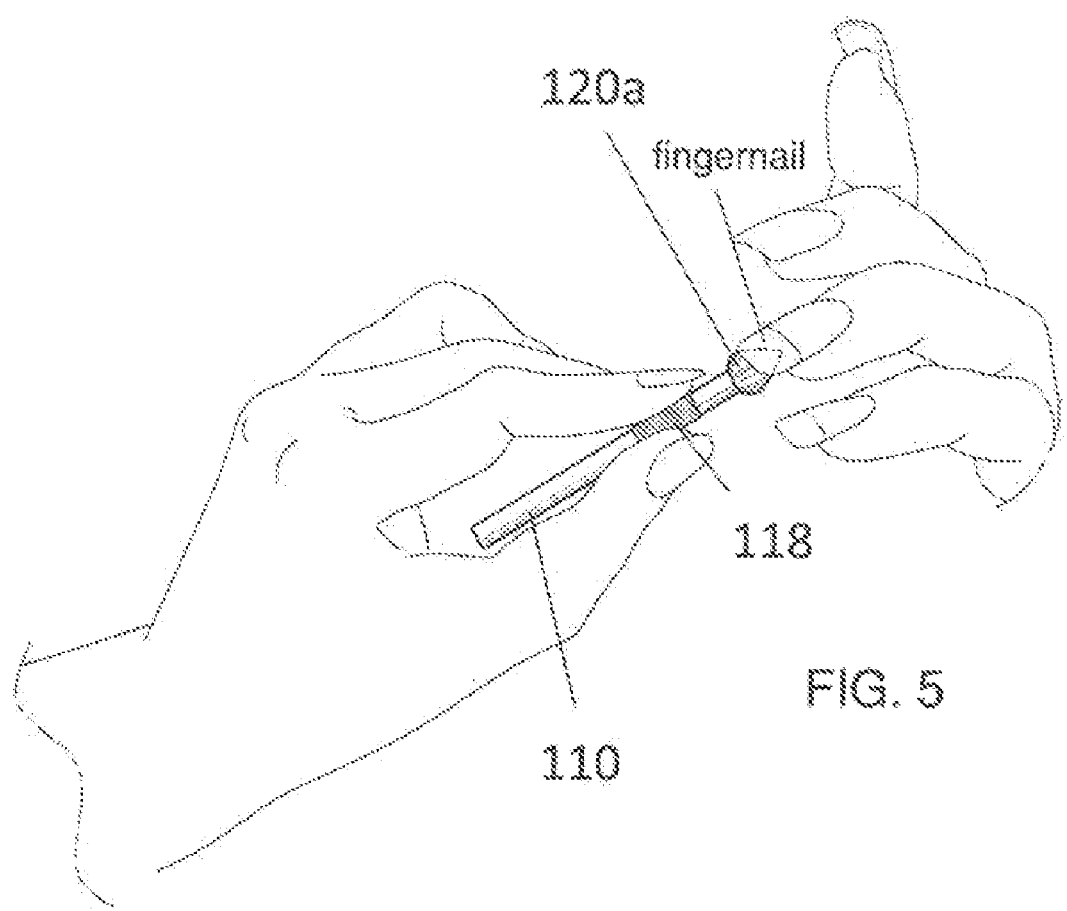
FIG. 5 is an in-use view of the swab of the present invention. To use the swab, simply sweep the absorbent component with the cleaning solution underneath the nail to help remove dirt and debris (and disinfect and seal).

As shown in FIG. 4, the absorbent component 120a may be attached to the first end of the shaft 110 via an adhesive 128. In some embodiments, a second absorbent component is disposed on the second end of the shaft 110.

The swabs 100 of the present invention may be constructed in a variety of shapes and sizes. For example, in some embodiments, the absorbent component 120a is generally rounded, flat, or a combination thereof. The present invention is not limited to the aforementioned shapes. In some embodiments, the shaft 110 is between about 1 to 2 inches in height as measured from the first end to the second end. In some embodiments, the shaft 110 is between about 2 to 3 inches in height as measured from the first end to the second end. In some embodiments, the shaft 110 is between about 3 to 5 inches in height as measured from the first end to the second end. In some embodiments, the shaft 110 is more than about 5 inches in height as measured from the first end to the second end.

As used herein, the term "about" refers to plus or minus 10% of the referenced number. For example, an embodiment wherein the shaft 110 is about 5 inches in height includes a shaft 110 that is between 4.5 and 5.5 inches in height.

The disclosures of the following U.S. patents are incorporated in their entirety by reference herein: U.S. Pat. No. 4,886,078; U.S. Pat. Application No. 2009/0183327; U.S. Pat. Application No. 200710113864; U.S. Pat. No. 1,667,570; U.S. Pat. No. 4,930,529; U.S. Pat. No. 1,956,627; U.S. Pat. No. 6,516,812;U.S. Pat. No. 6,102,048; U.S. Design Pat. No. D416,688; U.S. Pat. No. 1,367,974.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A cleaning solution consisting of keratin, equisetum arvense, carrageenan, Aucoumea klaineana extract, ginseng root extract, vitamin C, and tea tree oil, and the following amino acids (by volume): about 6.6% Aspartic Acid, about 14.2% Glutamic Acid, about 10.7% Serine, about 8.3% Glycine, about 0.7% Histidine, about 7% Argenine, about 6.4% Threonine, about 7.3% Alanine, about 6.6% Proline, about 1.6% Tyrosine, about 6.9% Valine, about 0.1% Methionine, about 0.5% Lanthionine, about 3.8% Isoleucine, about 8.8% Leucine, about 2.4% Phenylalanine, about 2.4% Lysine, and about 4.8% Cystine.

2. A cleaning swab comprising an elongated shaft having a first end and a second end; and a first absorbent component disposed on at least the first end of the elongated shaft, wherein the first absorbent component is impregnated with a solution consisting of keratin, equisetum arvense, carrageenan, Aucoumea klaineana extract, ginseng root extract, vitamin C, and tea tree oil, and the following amino acids (by volume): about 6.6% Aspartic Acid, about 14.2% Glutamic Acid, about 10.7% Serine, about 8.3% Glycine, about 0.7% Histidine, about 7% Argenine, about 6.4% Threonine, about 7.3% Alanine, about 6.6% Proline, about 1.6% Tyrosine, about 6.9% Valine, about 0.1% Methionine, about 0.5% Lanthionine, about 3.8% Isoleucine, about 8.8% Leucine, about 2.4% Phenylalanine, about 2.4% Lysine, and about 4.8% Cystine.

3. The cleaning swab of claim 1 further comprising a gripping component disposed on the shaft.

4. The cleaning swab of claim 1 further comprising a second absorbent component disposed on the second end of the shaft.

* * * * *